US00PP20330P2

(12) United States Plant Patent
Snoeijer

(10) Patent No.: US PP20,330 P2
(45) Date of Patent: Sep. 22, 2009

(54) ***CLEMATIS* PLANT NAMED 'ZODAQUE'**

(50) Latin Name: ***Clematis* hybrid**
Varietal Denomination: Zodaque

(76) Inventor: Wim Snoeijer, Vest 162, 2801 TX Gouda (NL)

( * ) Notice: Subject to any disclaimer, the term of this patent is extended or adjusted under 35 U.S.C. 154(b) by 0 days.

(21) Appl. No.: 12/228,035

(22) Filed: Aug. 8, 2008

(51) Int. Cl.
*A01H 5/00* (2006.01)

(52) U.S. Cl. ..... Plt./228
(58) Field of Classification Search ..... Plt./228
See application file for complete search history.

*Primary Examiner*—June Hwu
(74) *Attorney, Agent, or Firm*—Penny J. Aguirre

(57) ABSTRACT

A new cultivar of hybrid *Clematis*, 'Zodaque', characterized by its free-flowering habit in summer with some re-bloom in summer, its upright facing, semi double pale purple flowers, its climbing growth habit, and its cold hardiness to U.S.D.A. Zone 6.

3 Drawing Sheets

Botanical classification: *Clematis* hybrid.
Variety denomination: 'Zodaque'.

CROSS REFERENCE TO A RELATED APPLICATION

This application is co-pending with a U.S. Plant Patent applications filed for a sibling derived from the same seedlot entitled *Clematis* Plant Named 'Zoklako' (U.S. Plant patent application Ser. No. 12/228,015).

BACKGROUND OF THE INVENTION

The present invention relates to a new and distinct cultivar of *Clematis*, botanically of hybrid origin and classified in the Patens Group, and will be referred to hereafter by its cultivar name, 'Zodaque'. 'Zodaque' is grown as an herbaceous climber for landscapes use or as a flowering potplant for the terrace.

'Zodaque' was selected as unique amongst a group of seedlings that the inventor grew for evaluation in his nursery in Boskoop, The Netherlands. The goal of the selection was to select a hardy climber with uniquely colored flowers that could be grown for different purposes in the garden. 'Zodaque' was selected by the inventor in summer of 2002 and derived from seeds collected in 1999 and sown in 2000 from open pollinated *Clematis* 'Silver Moon' (not patented).

Asexual reproduction of the new cultivar was first accomplished by internodial stem cuttings under the direction of the inventor in Boskoop, The Netherlands in 2002. The characteristics of this cultivar have been determined to be stable and are reproduced true to type in successive generations.

SUMMARY OF THE INVENTION

The following traits have been repeatedly observed and represent the characteristics of the new cultivar as grown outdoors for 5 years in Boskoop, The Netherlands. These attributes in combination distinguish 'Zodaque' from other cultivar of *Clematis* known to the inventor.

1. 'Zodaque' exhibits upright facing, semi-double flowers that are pale purple in color.

2. 'Zodaque' is free flowering in spring with additional flowering in summer.
3. 'Zodaque' exhibits a climbing growth habit.
4. 'Zodaque' is cold hardy to U.S.D.A. Zone 6.

'Zodaque' differs from its parent plant in having smaller flowers that are semi-double, 'Silver Moon' has single flowers. 'Zodaque' differs from its sibling selection, 'Zoklako', in flower color and in having semi-double flowers. 'Zoklako' has single flowers that have purple margins and centers that are white with purple veins. Close comparisons are *Clematis* 'Louise Rowe' and 'Belle of Woking' (both unpatented). 'Louise Rowe' differs from 'Zodaque' in having flowers that are larger, more violet-blue in color, and double with a ball-shape rather than spreading form. The summer flowers of 'Louise Rowe' are also single, rather than semi-double. 'Belle of Woking' differs from 'Zodaque' in having flowers that are larger, more violet in color, and summer blooms are rarely produced.

BRIEF DESCRIPTION OF THE DRAWING

The accompanying colored photographs illustrate the overall appearance and distinct characteristics of the new *Clematis*. The photographs were taken in May and July of a plant of 'Zodaque' as grown in a trial bed for 3 years in The Netherlands.

The photograph in FIG. 1 shows the flowering habit in spring.

Figure 1:
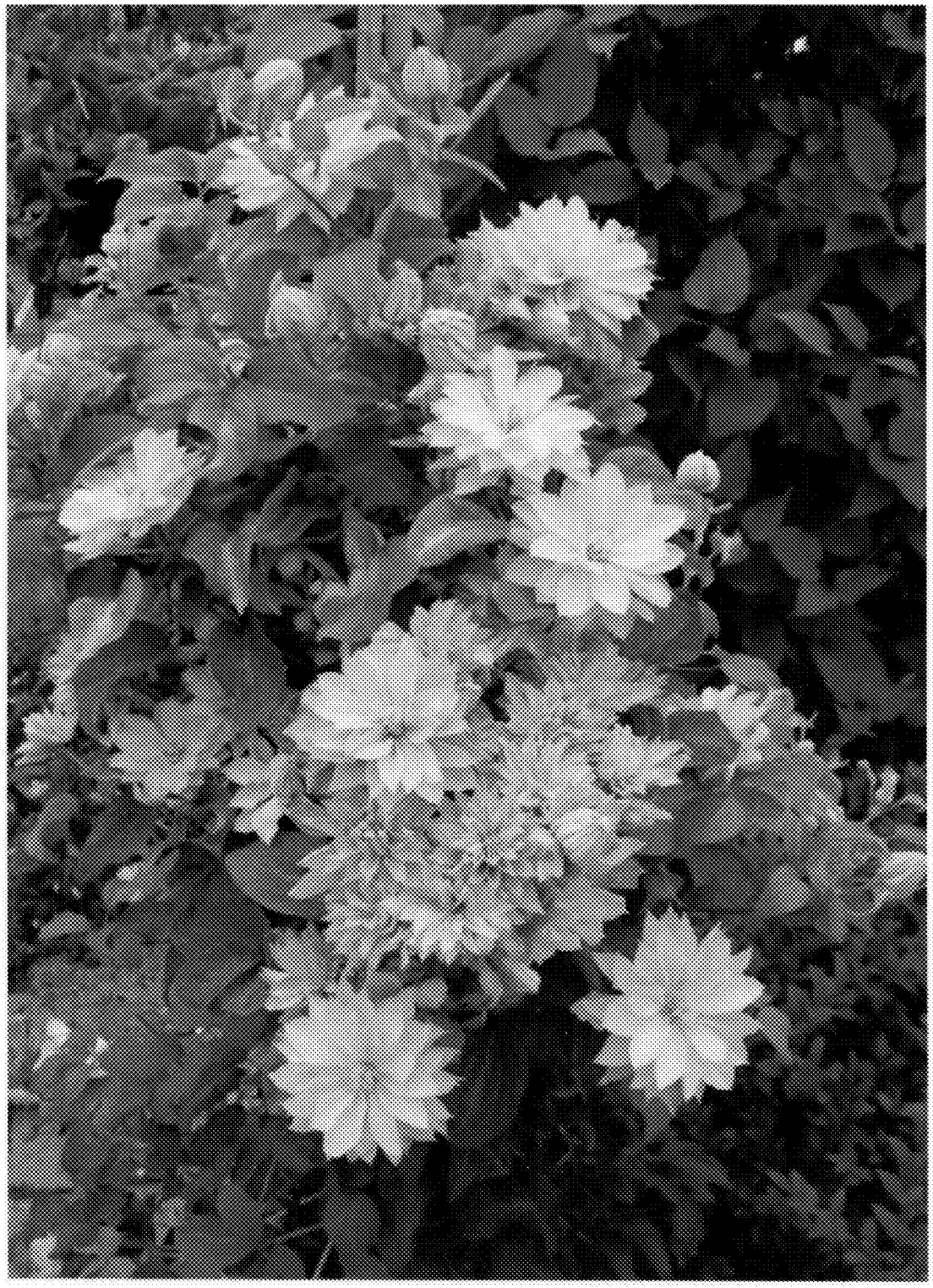
Figure 2:
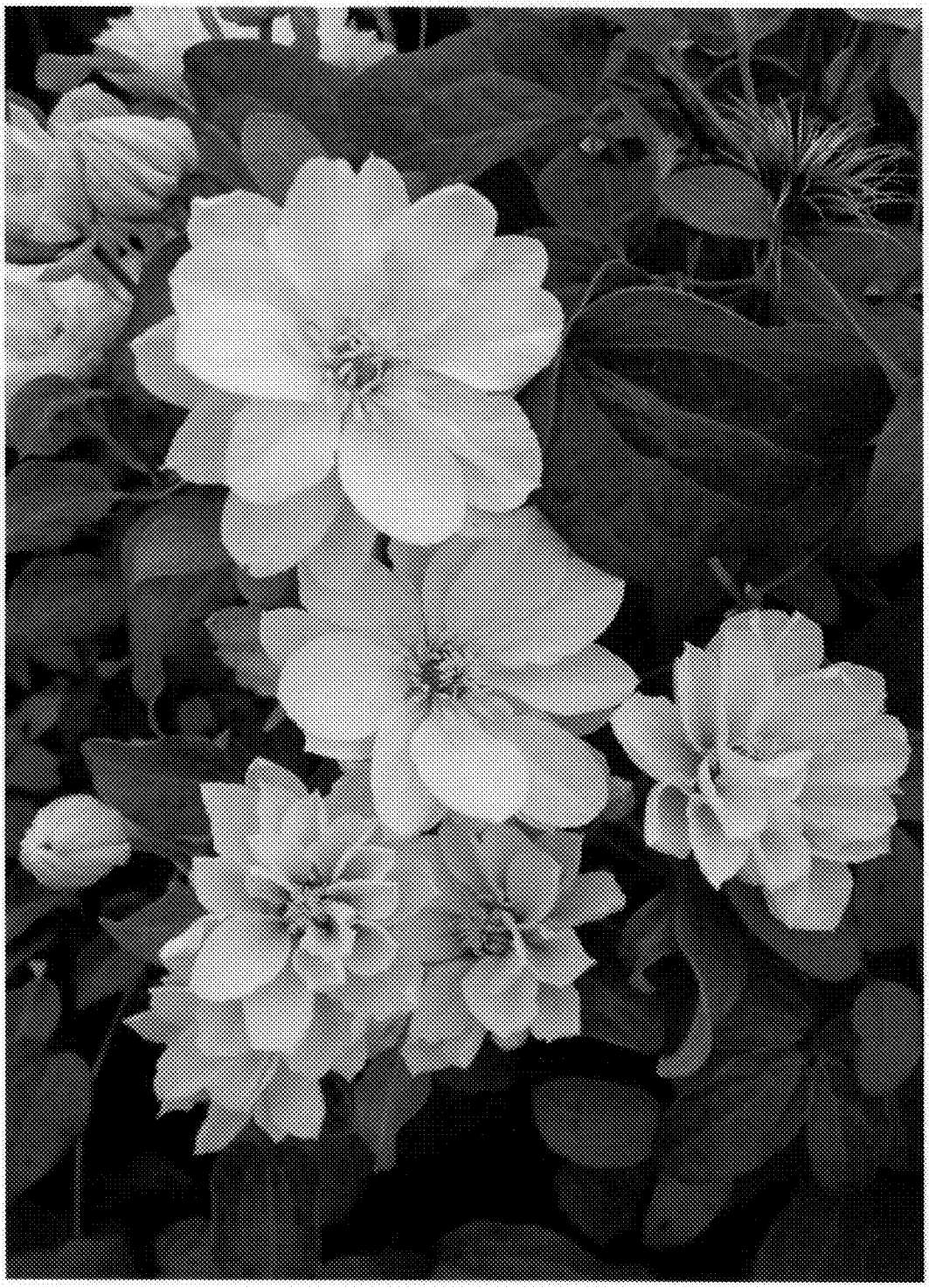
Figure 3:
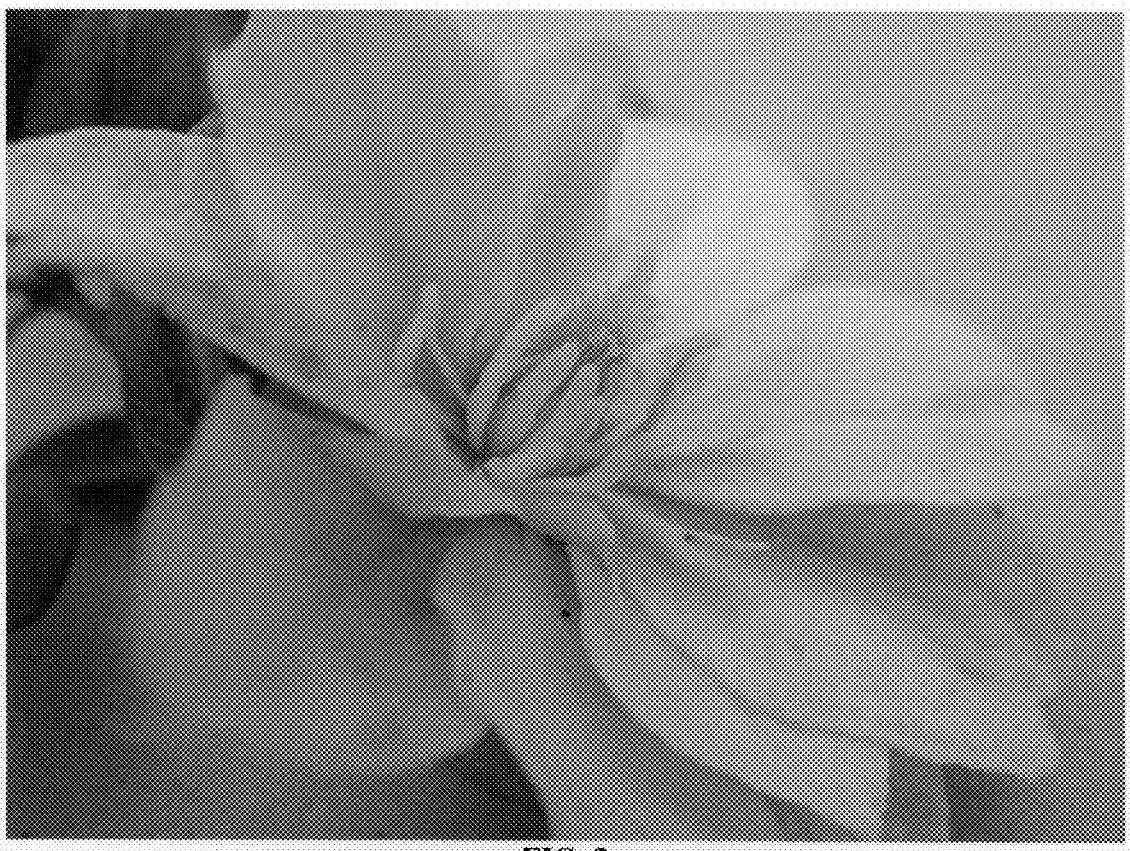

The photograph in FIG. 2 provides a close-up view of a flower in May and the photograph in FIG. 3 provides a close-up view of a flower in July.

Figure 4:
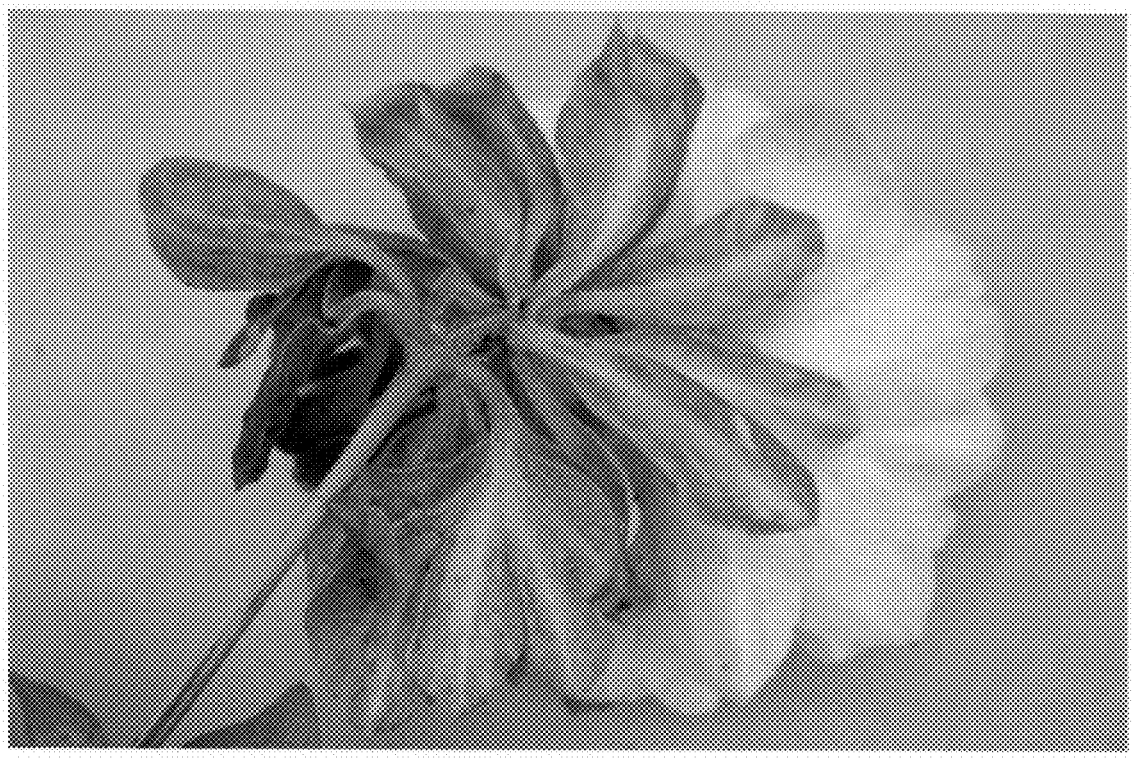

The photograph in FIG. 4 provides a close-up view of the bracts of a flower in July.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 3 year-old plants of 'Zodaque' as grown outdoors in full sun in a test plot in Boskoop, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Strong bloom for 4 to 6 weeks in spring with moderate re-bloom throughout the summer.

*Plant habit.*—Herbaceous climber.

*Height and spread.*—Three year-old plant is about 15 cm at base with a height of about 1.5 m when lightly pruned after spring flowering.

*Cold hardiness.*—U.S.D.A. Zone 6.

*Culture.*—Moist but well-drained soils in full sun with roots shaded.

*Diseases.*—No particular resistance to diseases has been observed.

*Root description.*—Fleshy.

Growth and propagation:

*Propagation.*—Internodial softwood cuttings from vegetative shoots.

*Root initiation.*—Roots develop in 6 weeks in summer under greenhouse conditions under intermittent mist without supplemental lighting.

*Time required for root development.*—75 to 90 days to develop a 5 cm container from a 5 cm cutting.

*Growth rate.*—Moderately vigorous once planted in the landscape.

Stem description:

*Shape.*—Round and 6 ribbed.

*Stem color.*—New growth is 146D and tinted with 166B on upper surface, matures quickly to 166A.

*Stem size.*—About 1.5 m (including peduncle and terminal pedicel) in length, average of 4.5 mm in diameter.

*Stem surface.*—Sparsely covered with very short hairs.

*Internode length.*—Ranges from 2 to 7 cm.

*Branching.*—Basal branching with lateral flowering branches at 50 to 100 cm from the base.

Foliage description:

*Leaf arrangement.*—Opposite.

*Leaf division.*—Ternate.

*Leaflet shape.*—Ovate.

*Leaflet base.*—Obtuse to cuneate.

*Leaflet apex.*—Obtuse.

*Leaflet fragrance.*—None.

*Leaflet venation.*—Moderately reticulate, not prominent, 144A in color.

*Leaflet margins.*—Entire.

*Leaflet attachment.*—Petioluled with leaf petioled.

*Leaflet surface.*—Glabrous on upper and lower surface.

*Leaflet size.*—Up to 5 cm in length and 2.5 cm in width.

*Leaflet color.*—Upper surface 147A, lower surface 147B.

*Petioles and petiolules.*—1 to 5 cm in length and about 1.5 mm in width, round in shape, 143C in color, sparsely hairy surface.

Inflorescence description:

*Inflorescence type.*—Solitary.

*Inflorescence arrangement.*—Terminal and axillary on young shoots.

*Peduncle.*—Average of 5 cm in length and an average of 2 mm in width, 143C in color, surface sparsely covered with short hairs, bracts; at base of flower, average of 12 per flower, simple, oblanceolate in shape (sometimes ternate), average 4 cm in length and 2 cm in width, pubescent on both surfaces, color same as leaflets.

*Bud description.*—Held upright, ovate in shape, up to 3.5 cm in length and 2.5 cm in width, 145D in color.

*Flower fragrance.*—None.

*Lastingness of flowers.*—Individual flowers last about 10 days, tepals are strongly caducous, removal of spend flowers encourages new flowers.

*Flower quantity.*—*About* 100 flowers on a 3 year-old plant.

*Flower type.*—Semi-double, spreading.

*Flower aspect.*—*Upright facing.*

*Flower size.*—Range from 5 to 8 cm in diameter and an average of about 4 cm in depth.

*Tepal number.*—10 to 30.

*Tepal shape.*—Elliptic.

*Tepal apex.*—Emarginate or acute or obtuse.

*Tepal base.*—Cunneate.

*Tepal margins.*—Entire.

*Tepal surface.*—Upper surface is glabrous, lower surface is glabrous with very short hairs towards middle area.

*Tepal color.*—Upper surface when open; 76C to N155A and tinted with 63D, upper surface when mature; 76C to N155A, lower surface when open and mature; 76D with a tint of 76B and center region 145D fading to 155A.

*Tepal size.*—Up to 4 cm in length and up to 1.5 cm in width.

Reproductive organs:

*Gynoecium.*—Numerous pistils (about 40), 1 cm in length, style is 155C in color and plumose, ovary is superior, hairy and N144C in color.

*Androcoecium.*—About 15, filaments are 2 to 5 mm in length and 1 mm in width, glabrous, and 155B in color, anthers are 3 mm in length and 4D in color with connective obtuse, glabrous and 155B in color, pollen is moderate in quantity and 8B in color.

*Seed.*—Seedheads are formed of drying stamens however seed production was not observed.

It is claimed;

1. A new and distinct cultivar of *Clematis* plant named 'Zodaque' as herein illustrated and described.

* * * * *